United States Patent [19]

Hoffman et al.

[11] Patent Number: 4,866,090
[45] Date of Patent: Sep. 12, 1989

[54] NOVEL HMG-COA REDUCTASE INHIBITORS

[75] Inventors: William F. Hoffman; Robert L. Smith; Ta J. Lee, all of Lansdale, Pa.

[73] Assignee: Merck & Co., Inc., Rahway, N.J.

[21] Appl. No.: 142,361

[22] Filed: Jan. 7, 1988

[51] Int. Cl.$^4$ .................. A61K 31/365; C07D 309/30
[52] U.S. Cl. .................. 514/460; 514/227.8; 514/231.5; 514/252; 514/319; 514/422; 544/60; 544/149; 544/374; 546/206; 548/517; 549/292; 549/264; 560/119
[58] Field of Search .................. 549/264, 292; 514/460

[56] References Cited

U.S. PATENT DOCUMENTS

| | | | |
|---|---|---|---|
| 4,351,844 | 9/1982 | Patchett et al. | 514/460 |
| 4,444,784 | 4/1984 | Hoffman et al. | 549/292 |
| 4,450,171 | 5/1984 | Hoffman et al. | 549/292 |
| 4,661,483 | 4/1987 | Hoffman et al. | 549/292 |

FOREIGN PATENT DOCUMENTS 0245003  11/1987  European Pat. Off. ............ 549/292

*Primary Examiner*—Glennon H. Hollrah
*Assistant Examiner*—Susan P. Treanor
*Attorney, Agent, or Firm*—Melvin Winokur; Joseph F. DiPrima

[57] ABSTRACT

Novel 3-hydroxy-3-methylglutaryl-coenzyme A (HMG-CoA) reductase inhibitors are useful as antihypercholesterolemic agents and are represented by the following general structural formulae (I) and (II):

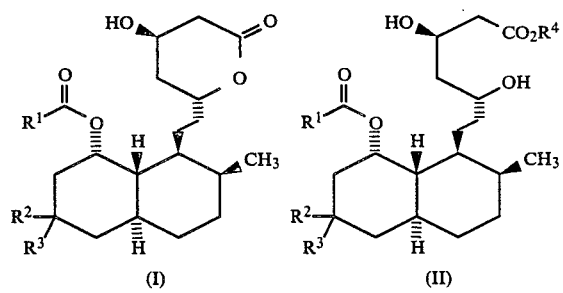

10 Claims, No Drawings

NOVEL HMG-COA REDUCTASE INHIBITORS

BACKGROUND OF THE INVENTION

Hypercholesterolemia is known to be one of the prime risk factors for atherosclerosis and coronary heart disease, the leading cause of death and disability in Western countries. The bile acid sequestrants seem to be moderately effective but they must be consumed in large quantities, i.e., several grams at a time, and they are not very palatable.

There are agents known, however, that are very active antihypercholesterolemic agents which function by limiting cholesterol biosynthesis via inhibiting the enzyme, HMG CoA reductase. These agents include the natural fermentation products, such as mevastatin, lovastatin and pravastatin, and semisynthetic analogs, such as simvastatin. These compounds have the following chemical structural formulae:

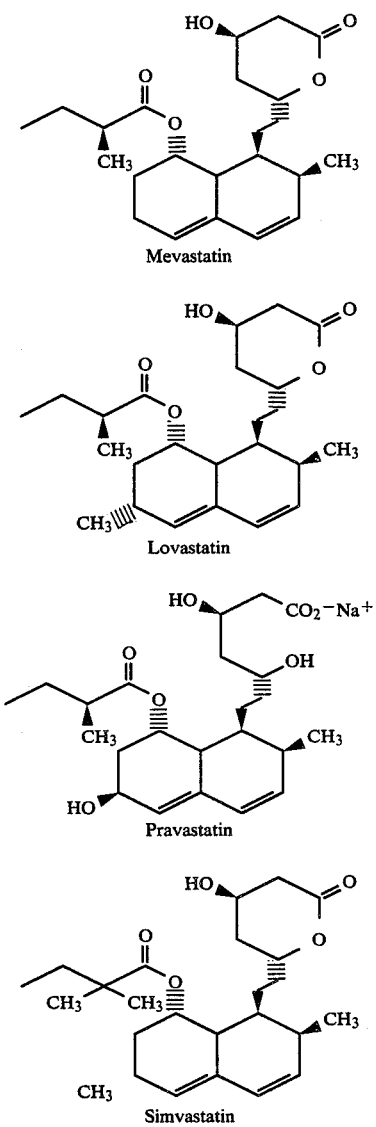

Recently, MEVACOR ®, which contains lovastatin as the active agent, was approved by the Food and Drug Administration for use as an antihypercholesterolemic drug.

Numerous analogs and homologs of these compounds have been described in the patent literature. U.S. Pat. No. 4,444,784 discloses analogs of lovastatin which possess polyhydronaphthyl moieties and various 8-acyloxy groups attached thereto. U.S. Pat. No. 4,661,483 also discloses analogs of lovastatin wherein the 8-acyloxy group has been elaborated. Additionally, co-pending U.S. applications Ser. Nos. 859,513, 859,525, 859,530, 859,534, and 859,535 all filed on May 5, 1986, disclose further analogs of lovastatin which have functionalized 8-acyloxy groups. All of the lovastatin analogs, including simvastatin, which contain a 6-methyl group, have that substituent in the natural 6α (axial) configuration.

Co pending U.S. patent application, Ser. No. 048,136 filed May 15, 1987, discloses compounds which are analogs of lovastatin and related compounds which possess a hydroxymethyl group, acyloxymethyl group, carbamoyloxymethyl group, a carboxy group, an alkoxycarbonyl group or a carbamoyl group substituted on the 6-position of the polyhydronaphthyl moiety. The compounds in this application may possess a substituent in the 6-position in either the 6α or 6β stereochemical position.

Co pending U.S. patent application, Ser. No. 092,354 filed Sept. 2, 1987, discloses compounds which are analogs of lovastatin and related compounds which possess a methyl group in the 6-position in the 6β stereochemical position.

SUMMARY OF THE INVENTION

This invention relates to novel compounds which are HMG—CoA reductase inhibitors and are useful as antihypercholesterolemic agents. Specifically the compounds of this invention are analogs of lovastatin and related compounds which are gem-disubstituted in the 6-position of the polyhydronaphthyl moiety. Additionally, pharmaceutical compositions of these novel compounds, as the sole therapeutically active ingredient and in combination with bile acid sequestrants, are disclosed. Other embodiments of this invention are methods of treating disease conditions in which hypercholesterolemia is an etiological factor, and processes for preparing the novel compounds

DETAILED DESCRIPTION OF THE INVENTION

The specific HMG—CoA reductase inhibitors of this invention are the compounds represented by the following general structural formulae (I) and (II):

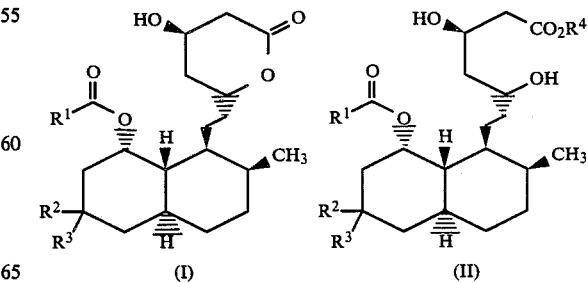

wherein:
$R^1$ is selected from:

(1) $C_{1-10}$ alkyl;
(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y,
  (i) $C_{1-10}$ alkylS(0)$_n$ in which n is 0 to 2,
  (j) $C_{3-8}$ cycloalkylS(0)$_n$,
  (k) phenylS(0)$_n$,
  (l) substituted phenylS(0)$_n$ in which the substituents are X and Y, and
  (m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
  (a) $C_{1-10}$ alkyl
  (b) substituted $C_{1-10}$ alkyl in which the substituent is selected from
    (i) halogen,
    (ii) hydroxy,
    (iii) $C_{1-10}$ alkoxy,
    (iv) $C_{1-5}$ alk oxycarbonyl,
    (v) $C_{1-5}$ acyloxy,
    (vi) phenyl,
    (vii) substituted phenyl in which the substituents are X and Y
    (viii) $C_{1-10}$ alkylS(0)$_n$,
    (ix) $C_{3-8}$ cycloalkylS(0)$_n$,
    (x) phenylS(0)$_n$,
    (xi) substituted phenylS(0)$_n$ in which the substituents are X and Y, and
    (xii) oxo,
  (c) $C_{1-10}$ alkylS(0)$_n$,
  (d) $C_{3-8}$ cycloalkylS(0)n,
  (e) phenylS(0)$_n$,
  (f) substituted phenylS(0)$_n$ in which the substituents are X and Y,
  (g) halogen,
  (h) hydroxy,
  (i) $C_{1-10}$ alkoxy,
  (j) $C_{1-5}$ *alkoxycarbonyl,*
  (k) $C_{1-5}$ acyloxy,
  (l) phenyl, and
  (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
  (a) piperidinyl,
  (b) pyrrolidinyl,
  (c) piperazinyl,
  (d) morpholinyl, and
  (e) thiomorpholinyl; and
(17) $R^6S$ in which $R^6$ is selected from
  (a) $C_{1-10}$ alkyl,
  (b) phenyl, and
  (c) substituted phenyl in which the substituents are X and Y;

$R^2$ and $R^3$ are independently selected from:
(1) $C_{1-10}$ alkyl; and
(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,or
(3) together with the carbon atom to which they are attached form a $C_{3-8}$ carbocyclic ring;

$R^4$ is selected from:
(1) hydrogen;
(2) $C_{1-5}$ alkyl;
(3) substituted $C^{1-5}$ alkyl in which the substituent is selected from
  (a) phenyl,
  (b) dimethylamino, and
  (c) acetylamino, and
(4) 2,3-dihydroxypropyl;

X and Y independently are hydrogen, halogen, trifluoromethyl, $C_{1-3}$ alkyl, nitro, cyano or group selected from:
(1) $R^8O(CH_2)_m$ in which m is 0 to 3 and $R^8$ is hydrogen, $C_{1-3}$alkyl or hydroxy $C_{2-3}$alkyl;
(2)

$$\overset{O}{\underset{\|}{R^9C}}O(CH_2)_m \text{ or } R^9O\overset{O}{\underset{\|}{C}}O(CH_2)_m$$

in which $R^9$ is hydrogen, $C_{1-3}$alkyl, hydroxy $C_{2-3}$alkyl, phenyl, naphthyl, amino-$C_{1-3}$alkyl, $C_{1-3}$alkylamino-$C_{1-3}$alkyl, di($C_{1-3}$alkyl)amino-$C_{1-3}$alkyl, hydroxy $C_{2-3}$ alkylamino-$C_{1-3}$alkyl or di(hydroxy-$C_{2-3}$alkyl) amino-$C_{1-3}$alkyl;
(3)

$$R^{10}O\overset{O}{\underset{\|}{C}}(CH_2)_m$$

in which $R^{10}$ is hydrogen, $C_{1-3}$alkyl, hydroxy-$C_{2-3}$ alkyl, $C_{1-3}$alkoxy $C_{1-3}$alkyl, phenyl or naphthyl;
(4)

$$R^{11}R^{12}N(CH_2)_m, \ R^{11}R^{12}N\overset{O}{\underset{\|}{C}}(CH_2)_m \text{ or } R^{11}R^{12}N\overset{O}{\underset{\|}{C}}O(CH_2)_m$$

in which $R^{11}$ and $R^{12}$ independently are hydrogen, $C_{1-3}$ alkyl, hydroxy-$C_{2-3}$alkyl or together with the nitrogen atom to which they are attached form a heterocyclic group selected from piperidinyl, pyrrolidinyl, piperazinyl, morpholinyl or thiomorpholinyl;

(5) $R^{13}S(O)_n(CH_2)_m$ in which $R^{13}$ is hydrogen, $C_{1-3}$alkyl, amino, $C_{1-3}$alkylamino or di($C_{1-3}$alkyl)amino;

or a pharmaceutically acceptable salt thereof.

Except where specifically defined to the contrary, the terms "alkyl", "alkoxy" and "acyl" include both the straight-chain and branched-chain species of the term.

One embodiment of this invention is the class of compounds of the formulae (I) and (II) wherein:

$R^1$ is selected from:
(1) $C_{1-10}$ alkyl;
(2) substituted $C_{1-10}$ alkyl in which one or more substituent(s) is selected from
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl
 (g) phenyl,
 (h) substituted phenyl in which the substituents are X and Y, and
 (i) oxo;
(3) $C_{3-8}$ cycloalkyl;
(4) substituted $C_{3-8}$ cycloalkyl in which one substituent is selected from
 (a) $C_{1-10}$ alkyl,
 (b) substituted $C_{1-10}$ alkyl in which the substituent is selected from
  (i) halogen,
  (ii) hydroxy,
  (iii) $C_{1-10}$ alkoxy
  (iv) $C_{1-5}$ acyloxy,
  (v) $C_{1-5}$ alkoxycarbonyl,
  (vi) phenyl,
  (vii) substituted phenyl in which the substituents are X and Y, and
  (viii) oxo,
 (c) halogen,
 (d) hydroxy,
 (e) $C_{1-10}$ alkoxy,
 (f) $C_{1-5}$ alkoxycarbonyl,
 (g) $C_{1-5}$ acyloxy,
 (h) phenyl,
 (i) substituted phenyl in which the substituents are X and Y;
(5) phenylamino;
(6) substituted phenylamino in which the substituents are X and Y;
(7) phenyl $C_{1-10}$ alkylamino; and
(8) substituted phenyl $C_{1-10}$ alkylamino in which the substituents are X and Y.

One subclass of this embodiment is the compounds of the formulae (I) and (II) wherein:

$R^1$ is selected from:
(1) $C_{1-10}$ alkyl;
(2) $C_{3-8}$ cycloalkyl;
(3) phenylamino; and
(4) substituted phenylamino in which the substituents are X and Y.

Illustrative of this subclass are those compounds of the formulae (I) and (II) wherein $R^2$ and $R^3$ are independently selected from:
(1) $C_{1-10}$ alkyl; and
(2) together with the carbon atom to which they are attached form a $C_{3-8}$ carbocyclic ring.

Exemplifying this subclass are the following compounds of the formulae (I) and (II):

(1) 6-(R)-[2-[8(S)-(2,2-dimethylbutyryloxy)-2(S),6,6-trimethyl-1,2,3,4,4a(S),5,6,7,8,8a(S)-decahydronaphthyl-1(S)]ethyl]-4(R)-hydroxy-3,4,5,6-tetrahydro-2H-pyran-2-one.

(2) 6(R)-[2-[8(S)-(2,2-dimethylbutyryloxy)-2(S)-methyl 6,6-dimethylene-1,2,3,4,4a(S),5,6,7,8,8a-(S)-decahydronaphthyl-1(S)]ethyl]-4(R)-hydroxy-3,4,5,-6-tetrahydro 2H-pyran 2-one and the corresponding ring opened dihydroxy acids and esters.

The compounds of formula (I) are conveniently prepared from 6(R)-[2-[8(S)-acyloxy-2(S)-methyl-6(S)-hydroxymethyl-1,2,3,4,4a(S),5,6,7,8, 8a(S)-decahydronaphthyl-1(S)]ethyl]-4(R)-trialkylsilyloxy-3,4,5,6-tetrahydro-2H-pyran-2-one, which may be prepared according to the general procedures described in co pending U.S. patent application, Ser. No. 015,637 filed Feb. 17, 1987, via the following synthetic pathway:

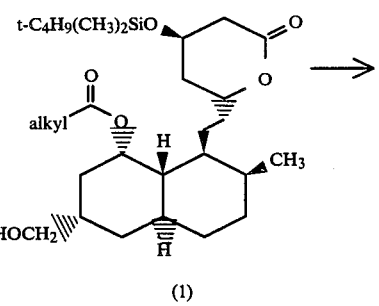

(1)

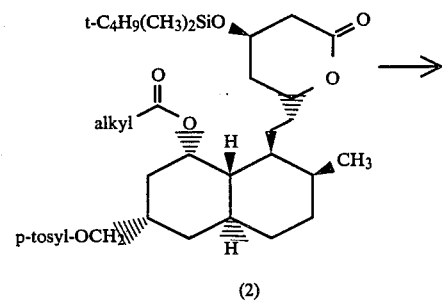

(2)

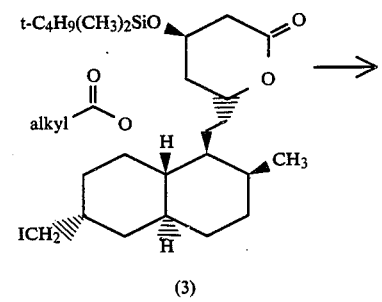

(3)

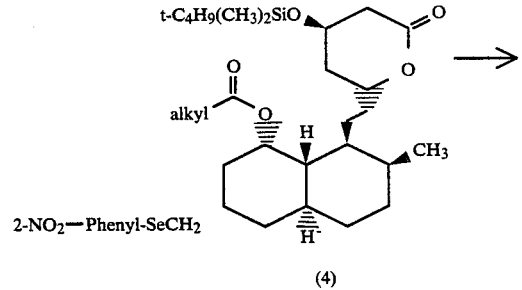

(4)

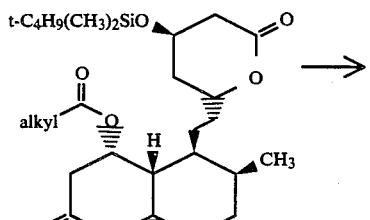

(5)

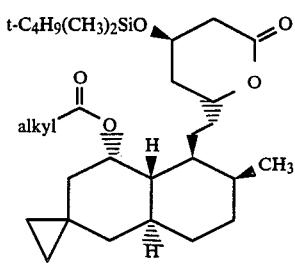

6(R)-[2-[8(S)-acyloxy-2(S) methyl-6(S)-hydroxymethyl-1,2,3,4,4a(S),5,6,7,8,8a(S)-decahydronaphthyl-1(S)]ethyl]-4(R)-triallkylsilyloxy-3,4,5,6-tetrahydro-2H-pyran-2-one, Compound 1, is treated with toluenesulfonyl chloride in a pyridine solution to give the 6-toluenesulfonyloxymethyl derivative, Compound 2. Compound 2 is then reacted with sodium iodide to give the 6-iodomethyl derivative, Compound 3, which is then added to a solution of 2-nitrophenylselenocyanate and sodium borohydride in a solvent to arrive at the 6-(2-nitrophenylselenomethyl) derivative, Compound 4. Treatment of Compound 4 with hydrogen peroxide yields the 6-exomethylene derivative, Compound 5.

The compounds of the formula (I) wherein $R^2$ and $R^3$ are both methyl or together are dimethylene are readily prepared from Compound 5 via the insertion of a methylene group into the exo double bond using diazomethane. Removal of the trialkylsilyl protecting group affords the desired 6,6-dimethylene product, which when hydrogenated yields the desired 6,6-dimethyl product.

Utilizing Compound 5, the 6,6-position of the compounds of formula (I) can be elaborated. Bromination of the exomethylene group leads to the 6-bromo,6-bromomethyl derivative which can be homologated using the standard reaction sequence of substitution with sodium cyanide, followed by basic hydrolysis to the carboxylic acid, acidification, relactonization, reduction to the corresponding diol and substitution to yield the dibromo analog which can be cyclized using malonic ester to yield the cycloalkyl derivative which can then be decarboxylated using standard techniques. Where the carbocyclic ring has an even number of carbon atoms, the 6,6-dimethylene product can be brominated to form the 6,6-bis(bromomethyl) derivative which can then be subjected to the standard homologation reaction sequence.

To obtain higher alkyl derivatives at the 6,6-positon of the polyhydronaphthyl ring, the intermediates of the above noted homologation reaction sequence can be modified utilizing standard chemical transformations. To obtain the substituted alkyl derivatives at the 6,6-position of the polyhydronaphthyl ring, Compound 5 can be reacted with a functionalized carbene, such as an alkoxycarbonylcarbene.

Where the reaction conditions of the above noted chemical transformations would be deleterious to the substituents contained in $R^1$, the acetoxy group can be employed as a protecting group which after the elaboration of the 6,6-positions can be removed by hydrolysis to give the 8-hydroxy derivative which then can be acylated according to the general procedures described in U.S. Pat. No. 4,661,483 and co pending U.S. application Ser. Nos. 859,513, 859,524, 859,525, 859,530, 859,534, and 859,535 all filed on May 5, 1986.

Where the product formed by the above described synthetic pathways is not the desired form of that compound, then that product may be subjected to one or more further reactions such as hydrolysis, salification, esterification, acylation, ammonolysis or lactonization by conventional methods, as described in more detail hereafter.

Preferred metal salts are salts with alkali metals, such as sodium or potassium, salts with alkaline earth metals, such as calcium, or salts with other metals such as magnesium, aluminum, iron, zinc, copper, nickel or cobalt, of which the alkali metal, alkaline earth metal, magnesium and aluminum salts are preferred, the sodium, calcium and aluminum salts being most preferred.

Preferred amino acids to form amino acid salts are basic amino acids, such as arginine, lysine, histidine, α,β-diaminobutyric acid or ornithine.

Preferred amines to form amine salts include t-octylamine, dibenzylamine, dichlorohexylamine, morpholine, alkyl esters of D-phenylglycine and D-glucosamine. Also preferred is ammonia to form the ammonium salt.

Esters are preferably the alkyl esters, such as the methyl, ethyl, propyl, isopropyl, butyl, isobutyl or pentyl esters, of which the methyl ester is preferred. However, other esters such as phenyl-$C_{1-5}$alkyl, dimethylamino-$C_{1-5}$alkyl, or acetylamino $C_{1-5}$alkyl may be employed if desired.

Metal salts of the carboxylic acids of formula (II) may be obtained by contacting a hydroxide, carbonate or similar reactive compound of the chosen metal in an aqueous solvent with the carboxylic acid of formula (II). The aqueous solvent employed is preferably water, or it may be a mixture of water with an organic solvent, preferably an alcohol (such as methanol or ethanol), a ketone (such as acetone), an aliphatic ether (such as THF) or an ester (such as ethyl acetate). It is preferred to use a mixture of a hydrophilic organic solvent with water. Such reactions are normally conducted at ambient temperature but they may, if desired, be conducted with heating or cooling.

Amine salts of the carboxylic acids of formula (II) may be obtained by contacting an amine in an aqueous solvent with the carboxylic acid of formula (II). Suitable aqueous solvents include water and mixtures of water with alcohols (such as methanol or ethanol), ethers (such as tetrahydrofuran), nitriles (such as acetonitrile) or ketones (such as acetone); it is preferred to use aqueous acetone as the solvent for this reaction. The reaction is preferably carried out at a temperature of ambient or below, more preferably a temperature of from 5° to 10° C. The reaction immediately goes to completion.

Amino acid salts of the carboxylic acids of formula (II) may be obtained by contacting an amino acid in aqueous solution with the carboxylic acid of formula (II). Suitable aqueous solvents include water and mixtures of water with alcohols (such as methanol or ethanol) or ethers (such as tetrahydrofuran).

Esters, preferably alkyl esters, of the carboxylic acids of formula (II) may be obtained by contacting the carboxylic acid of formula (II) with an appropriate alcohol, preferably in the presence of an acid catalyst, for example a mineral acid (such as hydrochloric acid or sulphuric acid), a Lewis acid (for example boron trifluoride) or an ion exchange resin. The solvent employed for this reaction is not critical, provided that it does not adversely affect the reaction; suitable solvents include benzene, chloroform, ethers and the like. Alternatively, the desired product may be obtained by contacting the carboxylic acid of formula (II) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (II) with a halide, preferably an alkyl halide, in a suitable solvent; preferred solvents include dimethylformamide, tetrahydrofuran, dimethylsulfoxide and acetone. All of the reactions for producing esters are preferably effected at about ambient temperature, but, if required by the nature of the reaction system, the reactions may be conducted with heating or cooling.

Lactones of the carboxylic acids of formula (I) may be obtained by lactonizing the carboxylic acids of formula (II) under ordinary conditions known to one skilled in the art.

The intrinsic HMG-CoA reductase inhibition activity of the claimed compounds is measured in the *in vitro* protocol published in *J. Med. Chem.*, 28, p. 347–358 (1985).

For estimation of relative inhibitory potencies, compactin (i.e., mevastatin) was assigned a value of 100 and the $IC_{50}$ value of the test compound was compared with that of compactin determined simultaneously in the published in vitro protocol.

Representative of the intrinsic HMG—CoA reductase inhibitory activities of the claimed compounds are the relative potencies tabulated below for several of the claimed compounds.

| $R^1$ | $R^2$ | $R^3$ | Relative Potency |
|---|---|---|---|
| 1,1-dimethylpropyl | $CH_3$ | $CH_3$ | 111 |
| 1,1-dimethylpropyl | —$CH_2CH_2$— | | 170 |

The compounds of this invention are useful as antihypercholesterolemic agents for the treatment of arteriosclerosis, hyperlipidemia, familial hypercholesterolemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 10 mg to 2000 mg (preferably 10 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)imino trimethylene dihalide]. The relative amounts of the compounds of this invention and these polymers is between 1:100 and 1:15,000.

Included within the scope of this invention is the method of treating arteriosclerosis, familial hypercholesterolemia or hyperlipidemia which comprises administering to a subject in need of such treatment a nontoxic, therapeutically-effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1 preparation of 6(R)-[2-(8(S)-(2,2-Dimethylbutyryloxy)-2(S),6,6-trimethyl-1,2,3,4,4a(S),5,6,7,8,8a(S)-decahydronaphthyl-1(S)]ethyl]-4(R) hydroxy-3,4,5,6-tetrahydro-2H pyran-2-one (8)

Step 1: Preparation of 6(R)-[2-(8(S)-(2,2-dimethylbutyryloxy)-2(S)-methyl-6(S)-[(4-methylphenyl)sulfonyloxymethyl]1,2,3,4,4a(S),5,6,7,8,8a(S)-decahydronaphthyl-1(S)]ethyl]-4(R)-(tert-butyldimethylsilyloxy)-3,4,5,6-tetrahydro-2H-pyran-2-one (2)

p-Toluenesulfonyl chloride (621 mg, 3.25 mmol) was added to a pyridine solution (20 ml) containing 6(R)-[2-(8(S)-(2,2-dimethylbutyryloxy)-2(S)-methyl-6(S)-hydroxymethyl-1,2,3,4,4a(S),5,6,7,8, 8a(S)-decahydronaphthyl-1(S)]ethyl]-4(R)-(tert-butyldimethylsilyloxy)-3,4,5,6-tetrahydro-2H-pyran-2-one (900 mg, 1.63 mmol) and 4-pyrrolidinopyridine (48 mg, 0.32 mmol) and the reaction mixture was stirred under ambient conditions for 18 hours. The pyridine was removed in vacuo and the residue was dissolved in ether (100 ml). The ethereal solution was washed with 5% HCl (3×10 ml), brine (10 ml), saturated $NaHCO_3$ solution (10 ml), brine (2×10 ml) and dried ($MgSO_4$). Filtration and evaporation gave the tosylate 2 as a colorless solid which was purified by flash chromatography on a silica gel column. Elution with acetone/$CH_2Cl_2$ (1:49/v:v) provided the title compound as a colorless solid, m.p. 141°–151° C.; nmr ($CDCl_3$) δ 0.057 (3H, s), 0.066 (3H, s), 0.867 (9H, s), 1.11 (3H, s), 1.12 (3H, s), 2.45 (3H, s), 3.81 (H, dd, J=10 Hz, 4 Hz), 4.27 (2H, m), 4.54 (H, m), 5.10 (H, m), 7.34 (2H, d, J=8 Hz), 7.79 (2H, J=8 Hz).

Step 2: Preparation of 6(R)-[2-(8(S)-(2,2-dimethylbutyryloxy)-2(S)-methyl-6(S)-iodomethyl-1,2,3,4,4a(S),5,6,7,8,8a(S)-decahydronaphthyl-1(S)]ethyl]-4(R)-(tert butyldimethylsilyloxy)-3,4,5,6-tetrahydro-2H-pyran-2-one (3)

Sodium iodide (138 mg, 0.92 mmol) was added to a DMF solution (10 ml) containing the tosylate 2 from Step 1 (130 mg, 0.183 mmol). After stirring at 100° C. (oil bath) for 18 hours, more sodium iodide (138 mg, 0.92 mmol) was added and heating was continued for an additional 6 hours. The solvent was removed in vacuo and the residue was dissolved in a mixture of ether (100 ml) and water. The ethereal layer was washed with $H_2O$ (2×25 ml) and dried ($MgSO_4$). Filtration and evaporation provided the title compound as a yellow oil which was used in Step 3 without further purification; nmr ($CDCl_3$) δ 6 0.072 (3H, s), 0.078 (3H, s), 0.88 (9H, s), 1.16 (3H, s), 1.18 (3H, s), 3.36 (H, dd, J=6 Hz, 6 Hz), 3.45 (H, dd, J=6 Hz, 6 Hz), 4.28 (H, m), 4.56 (H, m), 5.18 (H, m).

Step 3: Preparation of 6(R)-[2-(2(S)-2,2-dimethyl-butyryloxy)-2(S)-methyl-6(S)-[(2-nitrophenyl)-selenomethyl]-1,2,3,4,4a(S),5,6,7,8,8a (S)-decahydronaphthyl-1(S)]ethyl]-4(R)-(tert-butyldimethyl-silyloxy)-3,4,5,6-tetrahydro-2H-pyran-2-one (4)

Sodium borohydride (20 mg, 0.53 mmol) was added to a magnetically stirred suspension of 2-nitrophenyl-selenocyanate (120 mg, 0.53 mmol) in DMF (5 ml). After stirring the red solution for 15 minutes; a DMF solution (5 ml) of the iodo compound 3 from Step 2 (320 mg, 0.48 mmol) was added and the reaction mixture was stirred under ambient conditions for 10 hours. The reaction mixture was added to ether (100 ml) and the ethereal layer was washed with $H_2O$ (3×15 ml) and dried ($MgSO_4$). Filtration and evaporation provided a yellow oil which was purified by flsh chromatography on a silica gel column. Elution with ethyl acetate/hexane (1:3/v:v) gave starting material 3 followed by the title compound 4 as a pale yellow oil; nmr ($CDCl_3$) δ 0.074 (6H, s), 0.88 (9H, s), 1.16 (3H, s), 1.17 (3H, s), 3.11 (2H, m), 4.27 (H, m), 4.55 (H, m), 5.26 (H, m), 7.31 (H, m), 7.49 (3H, m), 8.28 (H, d, J=8 Hz).

Step 4: Preparation of 6(R)-[2-(8(S)-2,2-dimethyl-butyryloxy)-2(S)-methyl-6-methylene-1,2,3,4, 4a(S),5,6,7,8,8a(S)-decahydronaphthyl-1(S)]ethyl]-4(R) (tert-butyldimethylsilyloxy)-3,4, 5,6-tetrahydro-2H-pyran-2-one (5)

A THF solution (10 ml) containing compound 4 from Step 3 (98 mg, 0.133 mmol) and 30% $H_2O_2$(114 μ,1, 1.33 mmol) was stirred under a nitrogen atmosphere at room temperature for 18 hours. The red reaction mixture was poured into ether and the ethereal layer was washed with $H_2O$ (20 ml) saturated $NaHCO_3$ solution (10 ml), brine (2×10 ml) and dried ($MgSO_4$). Filtration and evaporation gave a red viscous oil which was purified by flash chromatography on a silica gel column. Elution with ethyl acetate/hexane (1:5.67/v:v) provided the title compound as a pale yellow oil; nmr ($CDCl_3$) δ 0.074 (3H, s), 0.078 (3H, s), 0.88 (9H, s), 1.12 (6H, s), 4.28 (H, m), 4.55 (H, m), 4.58 (H, m), 4.69 (H, m), 5.12 (H, m).

Step 5: Preparation of 6(R)-[2-(8(S)-2,2-dimethyl-butyryloxy)-2(S)-methyl-6,6-dimethylene-1,2,3,4,4a(S),5,6,7,8,8a(S)-decahydronaphthyl-1(S)]ethyl]-4(R)-(tert butyldimethylsilyloxy)-3,4,5,6-tetrahydro-2H-pyran-2-one (6)

Palladium acetate (10 mg, 0.044 mmol) was added to a cold (0°–5° C.) magnetically stirred ethereal solution (100 ml) containing compound 5 from Step 4 (107 mg, 0.20 mmol) and diazomethane (approx. 800 mg, 19 mmol). Additional palladium acetate (10 mg, 0.044 mmol) was added after 10 minutes and again after 20 minutes and the reaction mixture was stirred for a total of 30 minutes and filtered The filtrate was evaporated in vacuo to give a yellow oil which was purified by flash chromatography on silica gel. Elution with ethyl acetate/hexane (1:4/v:v) provided the title compound as a colorless oil; nmr ($CDCl_3$) δ 0.067 ( 3H, s), 0.073 (3H, s), 0.15 (2H, m), 0.28 (2H, m), 0.88 (9H, s), 1.16 (3H, s), 1.18 (3H, S), 4.27 (H, m), 4.56 (H, m), 5.12 (H, m).

Step 6: Preparation of 6(R)-[2-(8(S)-2,2-dimethyl-butyryloxy)-2(S)-methyl 6,6-dimethylene-1,2,3,4,4a(S),5,6,7,8,8a(S)-decahydronaphthyl-1(S)]ethyl]-4(R)-hydroxy-3,4,5,6-tetrahydro-2H-pyran-2-one (7)

A solution of 48% aqueous HF/$CH_3CN$ (1:19/v:v, 10 ml) was added to a $CH_3CN$ solution (2 ml) of the silyl ether 6 from Step 5 (110 mg, 0.20 mmol). After stirring 1.5 hours under ambient conditions the reaction soluton was poured into ether (100 ml). The ethereal solution was washed with saturated $NaHCO_3$ solution (10 ml), brine (2×20 ml) and dried ($MgSO_4$). Filtration and evaporation provided a viscous oil which was purified by flash chromatography on a silica gel column. Elution with isopropanol/hexane (1:5.67/v:v) gave the title compound as a colorless solid which was crystallized from hexane to yield colorless needles melting at 140°–141° C.; nmr ($CDCl_3$) δ 0.14 (2H, m), 0.26 (H, m), 0.32 (H, m), 1.17 (3H, s), 1.18 (3H, s), 4.36 (H, m), 4.60 (H, m), 5.16 (H, m).

Analysis for $C_{26}H_{42}O_5$; C, 71.85; H, 9.74. Found: C, 72.20; H, 10.08.

Step 7: Preparation of 6(R)-[2-(8(S)-2,2-dimethyl-butyryloxy)-2(S),6,6-trimethyl-1,2,3,4,4a(S), 5,6,7,8,8a(S)-decahydronaphthyl-1(S)]ethyl]-4(R)-hydroxy-3,4,5,6-tetrahydro-2H-pyran 2 -one (8)

An acetic acid soluton (10 ml) of compound 7 from Step 6 (21 mg, 0.048 mmol) was hydrogenated over 20% $Pd(OH)_2$ (42 mg) at 1000 psi and 50° C. for 48 hours. The reaction mixture was filtered and the filtrate concentrated in vacuo to a yellow oil which was purifed by flash chromatography on a silica gel column. Elution with isopropanol/hexane (1:9/v:v) provided a mixture (1/1) of compounds 7 and 8 as a colorless oil (15 mg). This mixture was separated by HPLC [Altex $C_8$ column (10 mm×12 cm)]. Elution with $CH_3CN/H_2O$ (7:3/v:v) at a flow rate of 8 ml/ min gave compound 7 (elution time =9.3 min) and the title compound (elution time=11.8 minutes) as a colorless solid, m.p. 139°–142° C.; nmr ($CDCl_3$) δ 0.81 (3H, d, J=7 Hz), 0.85 (3H, t, J=7 Hz), 0.87 (3H, s), 1.00 (3H, s), 1.15 (3H, s), 1.16 (3H, s), 4.38 (H, m), 4.58 (H, m), 5.17 (H, m).

EXAMPLE 2-6

Utilizing the general procedures described in Example 1, the following compounds of the formula (I) are prepared from the appropriately substituted standing materials:

| Compound No. | $R^1$ | $R^2$ | $R^3$ |
|---|---|---|---|
| 9 | sec-butyl | $CH_3$ | $CH_3$ |
| 10 | sec-butyl | —$CH_2CH_2$— | |
| 11 | 1,1-dimethypropyl | $CH_3CH_2$ | $CH_3CH_2$ |
| 12 | 1,1-dimethylpropyl | —$(CH_2)_4$— | |
| 13 | cyclopropyl | —$CH_2CH_2$— | |

EXAMPLE 7

Preparation of Ammonium Salts of Compounds II

The lactone (1.0 mmol) from Example 1, Step 7, is dissolved with stirring in 0.1N NaOH (1.1 mmol) at ambient temperature. The resulting solution is cooled and acidified by the dropwise addition of 1N HCl. The resulting mixture is extracted with diethyl ether and the extract washed with brine and dried ($MgSO_4$). The $MgSO_4$ is removed by filtration and the filtrate saturated with ammonia (gas) to give a gum which solidified to provide the ammonium salt.

EXAMPLE 8

Preparation of Alkali and Alkaline Earth Salts of Compounds II

To a solution of 42 mg of lactone from Example 1, Step 7, in 2 ml of ethanol is added 1 ml of aqueous NaOH (1 equivalent). After one hour at room temperature, the mixture is taken to dryness in vacuo to yield the desired sodium salt.

In like manner, the potassium salt is prepared using one equivalent of potassium hydroxide, and the calcium salt, using one equivalent of CaO.

EXAMPLE 9

Preparation of Ethylenediamine Salts of Compounds II

To a solution of 0.50 g of the ammonium salt from Example 7 in 10 ml of methanol is added 75 ml of ethylenediamine. The methanol is stripped off under vacuum to obtain the desired ethylenediamine salt.

EXAMPLE 10

Preparation of Tris(hydroxymethyl)aminomethane Salts of Compounds II

To a solution of 202 mg of the ammonium salt from Example 7 in 5 ml of methanol is added a solution of 60.5 mg of tris(hydroxymethyl) aminomethane in 5 ml of methanol. The solvent is removed in vacuo to afford the desired tris(hydroxymethyl)aminomethane salt.

EXAMPLE 11

Preparation of L-Lysine Salts of Compounds II

A solution of 0.001 mole of L-lysine and 0.0011 mole of the ammonium salt from Example 7 in 15 ml of 85% ethanol is concentrated to dryness in vacuo to give the desired L-lysine salt.

Similarly prepared are the L-arginine, L-ornithine, and N-methylglucamine salts.

EXAMPLE 12

Preparation of Tetramethylammonium Salts of Compounds II

A mixture of 68 mg of ammonium salt from Example 7 in 2 ml of methylene chloride and 0.08 ml of 24% tetramethylammonium hydroxide in methanol is diluted with ether to yield the desired tetramethyl ammonium salt.

EXAMPLE 13

Preparation of Methyl Esters of Compounds II

To a solution of 400 mg of lactone from Example 1, Step 7, in 100 ml of absolute methanol is added 10 ml 0.1M sodium methoxide in absolute methanol. This solution is allowed to stand at room temperature for one hour, then is diluted with water and extracted twice with ethyl acetate. The organic phase is separated, dried ($Na_2SO_4$), filtered and evaporated in vacuo to yield the desired methyl ester.

In like manner, by the use of equivalent amounts of propanol, butanol, isobutanol, t butanol, amylalcohol, isoamylalcohol, 2,2-dimethylamino ethanol, benzylalcohol, phenethanol, 2-acetamido ethanol and the like, the corresponding esters are obtained.

EXAMPLE 14

Preparation of Free Dihydroxy Acids

The sodium salt of the compound II from Example 8 is dissolved in 2 ml of ethanol-water (1:1; v:v) and added to 10 ml of 1N hydrochloric acid from which the dihydroxy acid is extracted with ethyl acetate. The organic extract is washed once with water, dried ($Na_2SO_4$), and evaporated in vacuo with a bath temperature not exceeding 30° C. The dihydroxy acid derivative derived slowly reverts to the corresponding, parent lactone on standing.

EXAMPLE 15

As a specific embodiment of a composition of this invention, 20 mg of lactone from Example 1, Step 7, is formulated with sufficient finely divided lactose to provide a total amount of 580 to 590 mg to fill a size 0, hard gelatin capsule.

What is claimed is:

1. A compound represented by the following structural formula (I):

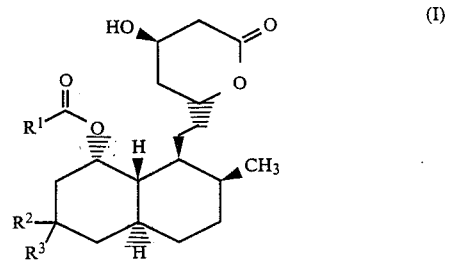

wherein:
  $R^1$ is selected from:
  (1) $C_{1-10}$ alkyl;
  (2) substituted $C_{1-10}$ alkyl in which one or more substituent(s) is selected from
    (a) halogen,
    (b) hydroxy,
    (c) $C_{1-10}$ alkoxy,
    (d) $C_{1-5}$ alkoxycarbonyl,
    (e) $C_{1-5}$ acyloxy,
    (f) $C_{3-8}$ cycloalkyl,
    (g) phenyl,
    (h) substituted phenyl in which the substituents are X and Y,
    (i) $C_{1-10}$ alkylS(0)n in which n is 0 to 2,
    (j) $C_{3-8}$ cycloalkylS(0)$_n$,
    (k) phenylS(0)$_n$,
    (l) substituted phenylS(0)$_n$ in which the substituents are X and Y, and
    (m) oxo;
  (3) $C_{1-10}$ alkoxy;
  (4) $C_{2-10}$ alkenyl;
  (5) $C_{3-8}$ cycloalkyl;
  (6) substituted $C_{3-8}$ cycloalkyl in which one substituent is selected from
    (a) $C_{1-10}$ alkyl
    (b) substituted $C_{1-10}$ alkyl in which the substituent is selected from
      (i) halogen,
      (ii) hydroxy,
      (iii) $C_{1-10}$ alkoxy,
      (iv) $C_{1-5}$ alkoxycarbonyl,
      (v) $C_{1-5}$ acyloxy, (vi) phenyl,
(vii) substituted phenyl in which the substituents are X and Y
(viii) $C_{1-10}$ alkylS(0)$_n$,
(ix) $C_{3-8}$ cycloalkylS(0)$_n$,
(x) phenylS(0)$_n$,
(xi) substituted phenylS(O)$_n$ in which the substituents are X and Y, and
(xii) oxo,
(c) $C_{1-10}$ alkylS(0)$_n$,
(d) $C_{3-8}$ cycloalkylS(0)$_n$,
(e) phenylS(0)$_n$,
(f) substituted phenylS(0)$_n$ in which the substituents are X and Y,
(g) halogen,
(h) hydroxy,
(i) $C_{1-10}$ alkoxy,
(j) $C_{1-5}$ alkoxycarbonyl,
(k) $C_{1-5}$ acyloxy,
(l) phenyl, and
(m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) $R^6S$ in which $R^6$ is selected from
(a) $C_{1-10}$ alkyl,
(b) phenyl, and
(c) substituted phenyl in which the substituents are X and Y;
$R^2$ and $R^3$ are independently selected from:
(1) $C_{1-10}$ alkyl; and
(2) substituted $C_{1-10}$ alkyl in which one or more substituent(s) is selected from
(a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl, or
(3) together with the carbon atom to which they are attached form a $C_{3-8}$ carbocyclic ring;
X and Y independently are hydrogen, halogen, trifluoromethyl, $C_{1-3}$ alkyl, nitro, cyano or group selected from:
(1) $R^8O(CH_2)_m$ in which m is 0 to 3 and $R^8$ is hydrogen, $C_{1-3}$ alkyl or hydrogen, $C_{2-3}$ alkyl;
(2)

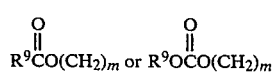

in which $R^9$ is hydrogen, $C_{1-3}$alkyl, hydroxy-$C_{2}$-alkyl, phenyl, naphthyl, amino $C_{1-3}$ alkyl, $C_{1-3}$ alkylamino-$C_{1-3}$ alkyl, di($C_{1-3}$alkyl)amino-$C_{1}$-alkyl, hydroxy $C_{2-3}$ alkylamino-$C_{1}$-alkyl or di(hydroxy $C_{2}$-alkyl) amino-$C_{1}$-alkyl;

(3)

$$R^{10}O\overset{O}{\overset{\|}{C}}(CH_2)_m$$

in which $R^{10}$ is hydrogen, $C_{1}$-alkyl, hydroxy-$C_{2-3}$ alkyl, $C_{1-3}$alkoxy-$C_{1-3}$alkyl, phenyl or naphthyl;
(4)

$$R^{11}R^{12}N(CH_2)_m, R^{11}R^{12}N\overset{O}{\overset{\|}{C}}(CH_2)_m$$

$$\text{or } R^{11}R^{12}N\overset{O}{\overset{\|}{C}}O(CH_2)_m$$

in which $R^{11}$ and $R^{12}$ independently are hydrogen, $C_{1-3}$ alkyl, hydroxy $C_{2-3}$alkyl;
(5) $R^{13}S(0)_n(CH_2)_m$ in which $R^{13}$ is hydrogen, $C_{1-3}$alkyl, amino, $C_{1-3}$alkylamino or di($C_{1-3}$alkyl)amino;
or a pharmaceutically acceptable salt thereof.

2. A compound of claim 1 wherein:
$R^1$ is selected from:
(1) $C_{1-10}$ alkyl;
(2) substituted $C_{1-10}$ alkyl in which one or more substituent(s) is selected from
(a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl,
(h) substituted phenyl in which the substitents are X and Y, and
(i) oxo;
(3) $C_{3-8}$ cycloalkyl;
(4) substituted C3-8 cycloalkyl in which one substituent is selected from
(a) $C_{1-10}$ alkyl,
(b) substituted $C_{1-10}$ alkyl in which the substituent is selected from
(i) halogen,
(ii) hydroxy,
(iii) $C_{1-10}$ alkoxy,
(iv) $C_{1-5}$ acyloxy,
(v) $C_{1-5}$ alkoxycarbonyl,
(vi) phenyl,
(vii) substituted phenyl in which the substituents are X and Y, and
(viii) oxo,
(c) halogen,
(d) hydroxy,
(e) $C_{1-10}$ alkoxy,
(f) $C_{1-5}$ alkoxycarbonyl,
(g) $C_{1-5}$ acyloxy,
(h) phenyl,
(i) substituted phenyl in which the substituents are X and Y;
(5) phenylamino;
(6) substituted phenylamino in which the substituents are X and Y;
(7) phenyl $C_{1-10}$ alkylamino; and (8) substituted phenyl $C_{1-10}$ alkylamino in which the substituents are X and Y.

3. A compound of claim 2 wherein:
$R^1$ is selected from:
(1) $C_{1-10}$ alkyl;
(2) $C_{3-8}$ cycloalkyl;
(3) phenylamino; and
(4) substituted phenylamino in which the substituents are X and Y.

4. A compound of claim 3 wherein:
$R^2$ and $R^3$ are independently selected from:
(1) $C_{1-10}$ alkyl; and
(2) together with the carbon atom to which they are attached form a $C_{3-8}$ carbocyclic ring.

5. A compound of claim 4 which is 6(R)-[2-[8(S)-(2,2-dimethylbutyryloxy)-2(S),6,6-trimethyl-1,2,3,4,4a(S),5,6,7,8,8a (S)-decahydronaphthyl-1(S)ethyl]-4(R)-hdroxy-3,4,5,6,-tetrahydro-2H-pyran-2-one.

6. A compound of claim 4 which is 6(R)-[2-[8(S)-(2,2-dimethylbutyryloxy)-2(S)-methyl-6,6dimethylene-1,2,3,4,4a (S),5,6,7,8,8a (S)-decahydronaphthyl-1(S)ethyl-4(R)-hydroxy-3,4,5,6-tetrahydro-2H-pyran-2-one.

7. A hypocholesterolemic, hypolipidemic pharmaceutical composition comprising a pharmaceutically acceptable carrier and a nontoxic effective amount of a compound as defined in claim 1.

8. A composition of claim 7 in which the compound is selected from:
(1) 6(R)-[2-[8(S)-(2,2-dimethylbutyryloxy)-2(S),6,6-trimethyl-1,2,3,4,4a(S),5,6,7,8,8a(S)-decahydronaphthyl-1(S)]ethyl]-4(R)-hydroxy-3,4,5,6-tetrahydro-2H-pyran-2-one;
(2) 6(R)-[2-[8(S)-(2,2-dimethylbutyryloxy)-2(S)-methyl-6,6-dimethylene-1,2,3,4,4a(S)5,6,7,8, 8a(S)-decahydronaphthyl-1(S)]ethyl]-4(R)-hydroxy-3,4,5 6-tetrahydro-2H-pyran-2-one.

9. A method of inhibiting cholesterol biosynthesis comprising the administration to a subject in need of such treatment a nontoxic therapeutically effective amount of a compound of claim 1.

10. A method of claim 9 in which the compound is selected from:
(1) 6(R)-[2-[8(S)-(2,2-dimethylbutyryloxy)-2(S)-methyl-6,6-dimethylene-1,2,3,4,4a(S)5,6,7,8, 8a(S)-decahtdronaphthyl-1(S)]ethyl]-4(R)-hydroxy-3,4,5 6-tetrahydro-2H-pyran-2-one.

* * * * *

UNITED STATES PATENT AND TRADEMARK OFFICE
CERTIFICATE OF CORRECTION

PATENT NO. : 4,866,090

DATED : September 12, 1989

INVENTOR(S) : W. F. Hoffman et al

It is certified that error appears in the above-identified patent and that said Letters Patent is hereby corrected as shown below:

At column 18, line 24, delete the period after 2-one and insert -- ; --.

At column 18, line 25, add --(2) 6(R) - [8(S)-(2,2-dimethylbutyryloxy)-2(S), 6,6-trimethyl-1,2,3,4,4a(S),5,6,7,8,8a(S)-decahydronaphthyl-1(S)]ethyl]-4(R)-hydroxy-3,4,5,6-tetrahydro-2H-pyran-2-one. --

Signed and Sealed this

Twenty-first Day of August, 1990

Attest:

HARRY F. MANBECK, JR.

*Attesting Officer*  *Commissioner of Patents and Trademarks*